United States Patent
Kwong et al.

(10) Patent No.: US 8,212,056 B2
(45) Date of Patent: Jul. 3, 2012

(54) LIGANDS FOR TRANSITION-METALS AND METHODS OF USE

(75) Inventors: Fuk Yee Kwong, Kowloon (CN); Chau Ming So, Kowloon (CN)

(73) Assignee: The Hong Kong Polytechnic University, Hong Kong (CN)

( * ) Notice: Subject to any disclaimer, the term of this patent is extended or adjusted under 35 U.S.C. 154(b) by 248 days.

(21) Appl. No.: 12/216,080

(22) Filed: Jun. 30, 2008

(65) Prior Publication Data

US 2009/0326243 A1   Dec. 31, 2009

(51) Int. Cl.
*C07F 9/02* (2006.01)
(52) U.S. Cl. ...................................................... 548/412
(58) Field of Classification Search .................. 548/111, 548/412
See application file for complete search history.

(56) References Cited

U.S. PATENT DOCUMENTS 6,307,087 B1   10/2001   Buchwald et al.

OTHER PUBLICATIONS

Jackstell et al., 2001, CAS: 136:199931.*
Wang et al., 1997, CAS: 126:317564.*
Musabekova et al., 1996, CAS: 125: 328441.*
Frenzel et al., 1996, CAS: 125:142846.*
Blanc et al., 2004, CAS: 140:390932.*
So et al., Organic Letters, 2007, 9(15): 2795-2798.*

* cited by examiner

*Primary Examiner* — Rei-tsang Shiao
(74) *Attorney, Agent, or Firm* — Wilkinson & Grist; George G. Wang (57) ABSTRACT

The present invention relates to indolyl phosphine ligands, and methods of making such ligands utilizing phenyl hydrazines and aryl ketones as the starting material. The present invention further includes uses of the ligands in the synthesis of pharmaceuticals, materials, and agriculture.

2 Claims, 3 Drawing Sheets

LIGANDS FOR TRANSITION-METALS AND METHODS OF USE

BACKGROUND

Transition-metal-catalyzed cross-coupling reactions have become an extremely versatile protocol in organic synthesis for the connection of two different fragments via the formation of either corban-carbon and/or carbon heteroatom bonds. The Suzuki reaction represents one of the most powerful methods of the construction of diversified biaryls, and they have a myriad of applications in pharmaceutical, materials, and agricultural chemistry. It has been recognized that the ligand employed in these processed has significant impact of the reactions. Hence, the strategic design of ligands with appropriate steric/electronic natures and great diversity is crucial in dealing with challenging and problematic substrates in this area.

Various observations and comments have been made that palladium complexes derived from sterically bulky and electron-rido phosphines are effective catalysts for C—C bond coupling processes from arylchlorides. Notably, the P+—$Bu_3$ by Fu and Koio, the ferrocenyl-based dialkylphosphines by Hortwing, biphenyl-based dialkylphosphines by Buchwald, and the heteroaromatic dialkylphosphines by Baller, are highly versitile.

It is one object of the present invention to teach a new ligands, as well as show methods of making such.

DESCRIPTION

The present invention relates to a class of indolyphosphine ligands prepared via Fischer indolization protocol. The ligands are prepared from phenylhydrazine and acetophenones as the starting material. The ligands are suitable for use as scaffolds in metal-ligand complexes, which can then serve as catalysts in further reactions. These ligands can be purified by single crystallization, and exhibit exceptionally high are stability in both solid and solution states.

These and other features, aspects, and advantages of the apparatus and methods of the present invention will become better understood from the following description, appended claims, and accompanying drawings where:

The following description of certain exemplary embodiment(s) is merely exemplary in nature and is in no way intended to limit the invention, its application, or uses. Throughout this description, the term "tunable" shall refer to the ability to design a chemical compound using to exhibit specific properties.

The present invention relates to indolyl phosphine ligands, and methods of making such utilizing phenylhydrazine and acetophenones as the starting material. The present invention further includes uses of the ligands in the synthesis of pharmaceuticals, materials, and agriculture.

The ligands of the present invention are generally of the structure 1, below:

(1)

wherein

Ar is selected from hydrogen, halogen, alkyl, alkenyl, alkynyl, hydroxyl, hydroxyl, alkoxyl, silgloxy, amino, nitro, sulfhydryl, alkylthio, imine, amide, phosphoryl, phosphonate, phosphine, carbonyl, carboxyl, carboxamide, anbydride, silyl, thioalkyl, alkylsulfonyl, arylsulfonyl, selenoalkyl, ketone, aldepyde, ester, heteroalkyl, nitrile gvanidine, amidine, acetal, ketal, amine oxide, aryl, heteroaryl, azide, aziridine, carbamate, epoxide, hydroxamic acid, imide, oxime, sulfonamide, thisamide, thiocarbamate, urea, or thiourea.

In one embodiment, Ar is selected from the group PH, H, 2-$MeC_6H_4$, 2-$MeOC_6H_4$, and 4$MeC_6H_4$.

R can be hydrogen, halogen, alkyl, alkenyl, hydroxyl, PH, Cy, and i-Pr.

In one embodiment, structure 2 is the synthesized ligand, (2)

wherein $R^1$ can be selected from hydrogen, halogen, alkyl, alkenyl, alkynyl, hydroxyl, alkoxyl, silyloxy, amine, nitro, sulfhydryl, alkylthio, imine, amide, phosphoryl, phosphonate, phosphine, carbonyl, carboxyl, carboxamide, anhydride, silyl, thioalkyl, alkyl sulfonyl, aryl sulfonyl, seleno alkyl, ketone, aldehyde, ester, heteroalkyl, nitrite guanidine, amidine, acetral, ketal, amineoxide, aryl, heteroryl, azide, aziridine, carbanonate, epoxide, hydroxamine acid, imide, oxime, sulfonamide, thioanide, thiocarbamate, urea, or thiourea.

R can be selected from H, 2-Me, 2-MeO, or 4-Me. Table 1 exhibits examples of selection combinations from R and $R^1$:

TABLE 1

|    | $R^1$  | R    |
|----|--------|------|
| a. | H      | Ph   |
| b. | H      | Cy   |
| c. | H      | i-Pr |
| d. | 2-Me   | Cy   |
| e. | 2-MeO  | Cy   |
| f. | 4-Me   | Cy   |

Figure 1:
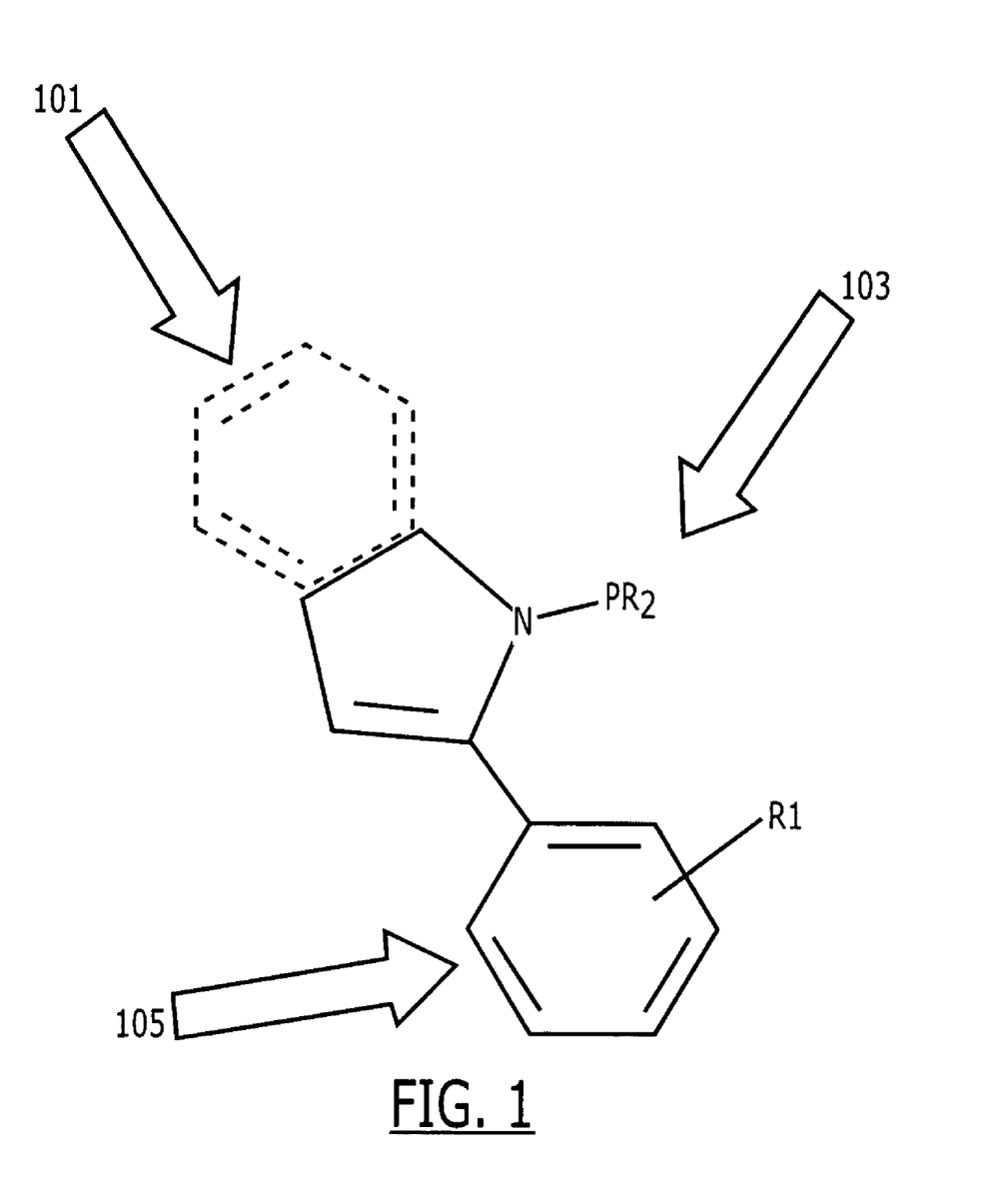
FIG. 1 shows the indolyl phosphine ligands of the present inventions.

The ligands of the present invention have benefits of being highly tunable. FIG. 1 exhibits tunable regions of the structure 2 ligand. The region 101 can provide ortho-steric hinderence by indolyl scaffold while minimizing ortho-steric hinderence by pyrroyl scaffold. Tunability can be obtained through the inclusion of Br, Cl, $CH_3$, $CH_2$, Fl, or $CH_3CH_2$. The region 103 shows potential steric and electronic fire tuning via substituents, including but not limited to PhyCy, or +/−Bu. The region 105 allows high ligand turnbility through the incorporation of different aryl rings.

The present invention also relates to the synthesis of the indolyl phosphine.

Figure 2:
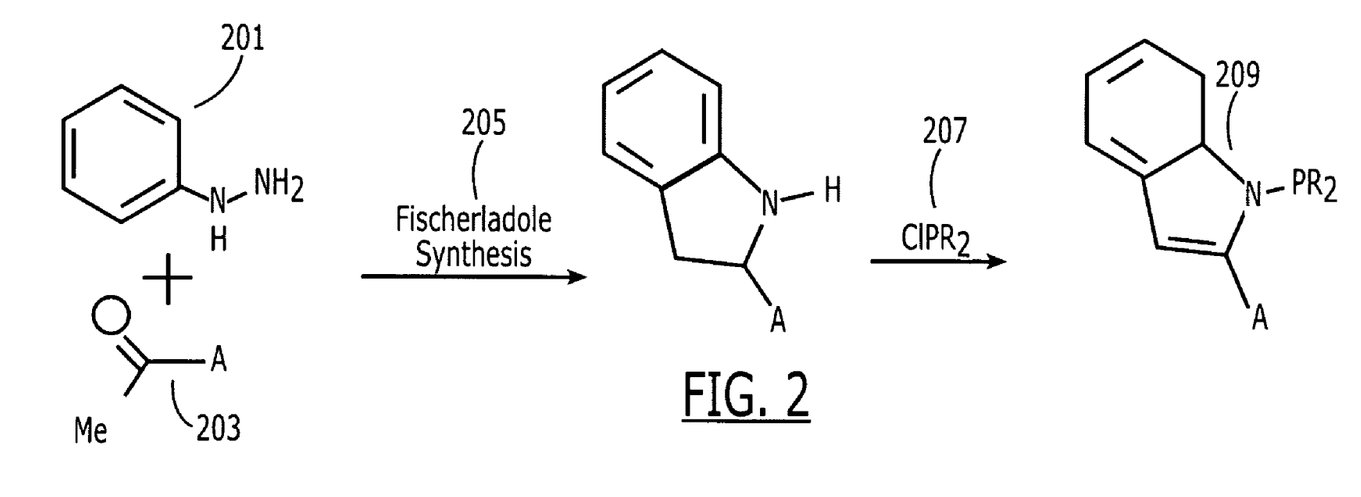
FIG. 2 shows a method of synthesizing the present ligands, in accordance of the present invention.

FIG. 2 exhibits the synthesis of the indolyl phosphine ligands, using a phenyl hydrazine 201 and an aryl ketone 203 as starting material.

Whereas phenyl hydrazine 201 is shown as the starting material, other suitable starting hydrazines include bromophenylhydrazine hydrochlorides, chlorophenyl hydrazine hydrochlorides, dimethylphenylhydrazine hydrochlorides, ethylphenylhydrazine hydrochlorides, or 1-methyl-1-phenylhydrazine.

Aryl ketones 203 can be selected from propiophenone, chalcone, acetophenone, benzophenone, dibenzoylmethane, 2-methylbenzophenone, 4-methylbenzophenone, phenyl-2-thienylmethanone, deoxybenzoin, crotonophenone, butyrophenone, 1-phenyl-1,2-proponedione, trans-chalcone, 2-propenophenone, dihydrochalcone, phenylxylyl ketone, and propyriophenone, The starting materials are subject to Fischer synthesis 205, which can occur under an acid selected from HCl, $H_2$, $So_4$, Polyphosphonine acid, Boron trifluoride, zinc chloride, or aluminum chloride, at an elevated temperature. The resultant intermediary is present in a yield of about 70% to 80%.

The intermediary is then subject to a phosphine compound 207. In one embodiment, the compound comprises Cl and an R compound. Cl can be substituted with Br, K, and the like. R can be represented by hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, lsetal, amine oxide, aryl, heteroaryl, azide, aziridine, carbonate, epoxide, hydroxamic acid, limide, oxime, sulfonamide, thioamide, thiocarbamate, urea, or thiourea.

The treatment of the intermediate results in an 80% to 90% yield of the indolyl phosphine ligand.

The phosphine ligands synthesized by the present invention are capable of serving as scaffolds for metal compounds, thus forming metal-complexes. Suitable metals includes nickel, platinum, or palladium. The metal complexes of the present invention are capable as serving as catalysts of a variety of applications in the pharmaceutical, material, and agricultural fields.

Figure 3:
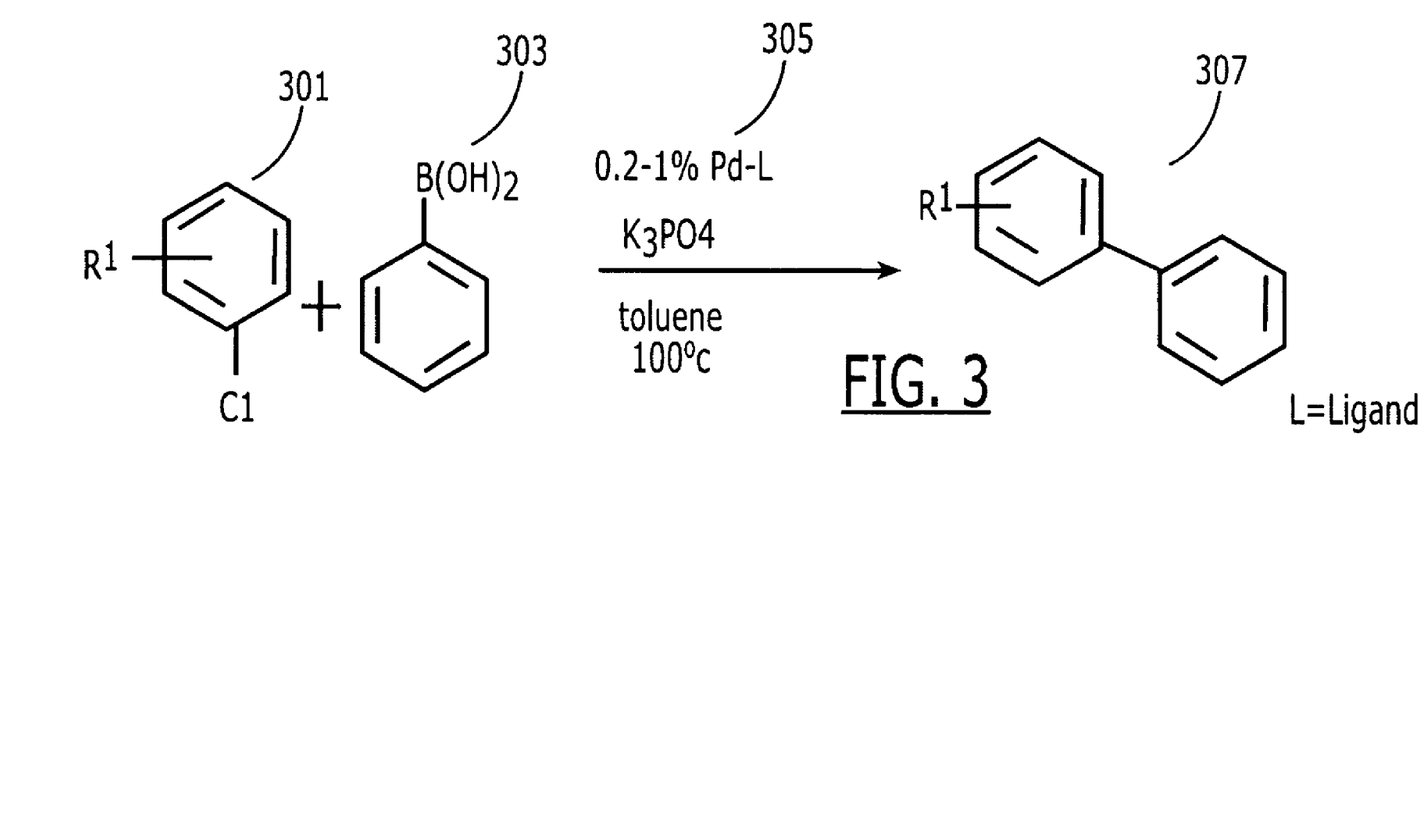
FIG. 3 exhibits a method of using the present ligands in a Suzuki reaction.

FIG. 3 shows an embodiment of the metal complexes of the present invention serving as a catalyst in a Suzuki reaction. As known in the art, a Suzuki reaction involves a reaction between an aryl- or vinyl-boronic acid and an aryl- or vinyl-halide. As shown in the embodiment, an aryl choride 301 is reacted with organoboron nucleophiles 303 including —B(oH)$_2$, —BF$_3$K, and —B(Pin). The catalyst is a palladium. Ligand complex 305 of the present invention. The palladium-ligand complex 305 can be used in a amount of 0.2 to 1%. The complex 305 is also used in conjunction with a base, such as $K_3PO_4$, $Cs_2CO_3$, CsF, and KO+—Bu. Due to the effectiveness of the complex 305 as a catalyst, yields of resultant compounds are as high as 90%.

Tables 2-8 exhibit several reactions utilizing the palladium-ligand complexes of the present invention, along with the resultant yields.

TABLE 2

| entry | ArCl | ArB(OH)$_2$ | product | mol % Pd | % yield* |
|---|---|---|---|---|---|
| 1 | Me-C6H4-Cl | (HO)$_2$B-C6H5 | Me-C6H4-C6H5 | 0.2% 24 h | 92 |
| 2 | 2-Me-C6H4-Cl | (HO)$_2$B-C6H5 | 2-Me-C6H4-C6H5 | 0.2% 24 h | 95 |

TABLE 2-continued

Pd-Ligand catalyzed Suzuki Reaction

| entry | ArCl | ArB(OH)₂ | product | mol % Pd | % yield* |
|---|---|---|---|---|---|
| 3 | 2-chlorotoluene | 4-methylphenylboronic acid | 2,4'-dimethylbiphenyl | 1% 24 h | 91 |
| 4 | 2,6-dimethylchlorobenzene | phenylboronic acid | 2,6-dimethylbiphenyl | 1% 24 h | 94 |
| 5 | 4-chlorobenzophenone | 2-methylphenylboronic acid | 2'-methyl-4-benzoylbiphenyl | 0.05% 16 h | 96 |
| 6 | 3-chloroaniline | 2-methylphenylboronic acid | 3-amino-2'-methylbiphenyl | 0.05% 24 h | 85 |
| 7 | 4'-chloroacetophenone | 1-naphthylboronic acid | 4-(1-naphthyl)acetophenone | 0.1% 16 h | 93 |
| 8 | methyl 4-chlorobenzoate | 4-methylphenylboronic acid | methyl 4'-methylbiphenyl-4-carboxylate | 0.02% 24 h | 96 |

TABLE 2-continued

Pd-Ligand catalyzed Suzuki Reaction

| entry | ArCl | ArB(OH)$_2$ | product | mol % Pd | % yield* |
|---|---|---|---|---|---|
| 9 | 3-Cl-C$_6$H$_4$-COOMe | 3,5-Me$_2$-C$_6$H$_3$-B(OH)$_2$ | methyl 3',5'-dimethylbiphenyl-3-carboxylate | 0.1% 16 h | 97 |
| 10 | 4-MeO-C$_6$H$_4$-Cl | PhB(OH)$_2$ | 4-methoxybiphenyl | 0.5% 24 h | 95 |
| 11 | 4-NC-C$_6$H$_4$-Cl | 1-naphthyl-B(OH)$_2$ | 4-(naphthalen-1-yl)benzonitrile | 0.05% 16 h | 96 |

TABLE 3

Pd-catalyzed amination of aryl mesylates

| entry | ArOMs | amine | product | mol % Pd | % yield[b] |
|---|---|---|---|---|---|
| 1 | 4-t-Bu-C$_6$H$_4$-OMs | PhNHMe | 4-t-Bu-C$_6$H$_4$-N(Me)Ph | 2%, 4 h | 93 |
| 2 | 4-t-Bu-C$_6$H$_4$-OMs | PhNHMe | 4-t-Bu-C$_6$H$_4$-N(Me)Ph | 0.6%, 24 h | 96 |
| 3 | 4-t-Bu-C$_6$H$_4$-OMs | 2,6-Me$_2$-C$_6$H$_3$-NH$_2$ | 4-t-Bu-C$_6$H$_4$-NH-(2,6-Me$_2$-C$_6$H$_3$) | 1%, 24 h | 90 |

TABLE 3-continued

Pd-catalyzed amination of aryl mesylates

| entry | ArOMs | amine | product | mol % Pd | % yield[b] |
|---|---|---|---|---|---|
| 4 | t-Bu-C6H4-OMs | HN(Ph)2 | t-Bu-C6H4-N(Ph)2 | 4%, 24 h | 80 |
| 5 | t-Bu-C6H4-OMs | morpholine | t-Bu-C6H4-morpholinyl | 1%, 18 h | 90 |
| 6[e] | t-Bu-C6H4-OMs | pyrrolidine | t-Bu-C6H4-pyrrolidinyl | 2%, 24 h | 93 |
| 7[e] | t-Bu-C6H4-OMs | HN(Bn)2 | t-Bu-C6H4-N(Bn)2 | 4%, 24 h | 81 |
| 8 | 3,5-Me2-C6H3-OMs | 2,6-Me2-C6H3-NH2 | 3,5-Me2-C6H3-N(Me)-2,6-Me2-C6H3 | 1%, 24 h | 67 |
| 9 | 2-naphthyl-OMs | pyrrolidine | 2-naphthyl-pyrrolidinyl | 2%, 24 h | 65 |
| 10 | 4-NC-C6H4-OMs | PhNHMe | 4-NC-C6H4-N(Me)Ph | 1%, 24 h | 82 |
| 11 | 4-MeO-C6H4-OMs | PhNH2 | 4-MeO-C6H4-NHPh | 2%, 24 h | 76 |
| 12[e] | 4-MsO-C6H4-Cl | PhNHMe | 4-MsO-C6H4-N(Me)Ph | 1%, 24 h | 89 |

TABLE 4

Pd-catalyzed N-arylation of nitrogen-heterocycles

| entry | ArOMs | N-heterocycle | product | mol % Pd | % yield[b] |
|---|---|---|---|---|---|
| 1 |  |  |  | 1%, 24 h | 93 |
| 2 |  |  |  | 1%, 20 h | 89 |
| 3 |  |  |  | 1%, 24 h | 96 |
| 4 |  |  |  | 2%, 24 h | 84 |
| 5 |  |  |  | 1%, 24 h | 80 |
| 6[c] |  |  |  | 2%, 24 h | 98 |
| 7 |  |  |  | 1%, 24 h | 86 |

TABLE 4-continued

Pd-catalyzed N-arylation of nitrogen-heterocycles

| entry | ArOMs | N-heterocycle | product | mol % Pd | % yield[b] |
|---|---|---|---|---|---|
| 8 |  |  |  | 1%, 24 h | 79 |

TABLE 5

Pd-catalyzed solventless amination of aryl mesylates

| entry | ArOMs | Amine | product | % yield[b] |
|---|---|---|---|---|
| 1 |  |  |  | 93 |
| 2 |  |  |  | 97 |
| 3 |  |  |  | 91 |
| 4 |  |  |  | 83 |

TABLE 6

Pd-catalyzed amination of aryl mesylates in aqueous medium

| entry | ArOMs | Amine | product | % yield[b] |
|---|---|---|---|---|
| 1 | t-Bu-C6H4-OMs | Me(H)N-Ph | t-Bu-C6H4-N(Me)-Ph | 90 |
| 2 | t-Bu-C6H4-OMs | 2,6-Me2-C6H3-NH2 | t-Bu-C6H4-NH-(2,6-Me2-C6H3) | 77 |
| 3 | 3,5-Me2-C6H3-OMs | 2,6-Me2-C6H3-NH2 | 3,5-Me2-C6H3-N(Me)-(2,6-Me2-C6H3) | 89 |
| 4 | 2-naphthyl-OMs | Me(H)N-Ph | 2-naphthyl-N(Me)-Ph | 86 |
| 5 | t-Bu-C6H4-OMs | indole (NH) | 1-(4-t-Bu-C6H4)-indole | 75 |

TABLE 7

Pd-catalyzed Suzuki-Miyaura coupling of ArOMs with Ar'B(OH)₂

| entry | ArOMs | Ar'B(OH)₂ | product | mol % Pd | % yield[b] |
|---|---|---|---|---|---|
| 1 | t-Bu-C6H4-OMs | PhB(OH)2 | 4-t-Bu-biphenyl | 1%, 19 h | 91 |
| 2 | t-Bu-C6H4-OMs | PhB(OH)2 | 4-t-Bu-biphenyl | 0.5%, 24 h | 88 |
| 3 | t-Bu-C6H4-OMs | 4-Me-C6H4-B(OH)2 | 4-t-Bu-4'-Me-biphenyl | 1%, 19 h | 90 |

TABLE 7-continued

Pd-catalyzed Suzuki-Miyaura coupling of ArOMs with Ar'B(OH)₂

| entry | ArOMs | Ar'B(OH)₂ | product | mol % Pd | % yield[b] |
|---|---|---|---|---|---|
| 4 |  |  |  | 3%, 8 h | 97 |
| 5 |  |  |  | 4%, 8 h | 70 |
| 6 |  |  |  | 2%, 3 h | 93 |
| 7 |  |  |  | 2%, 3 h | 52 |
| 8 |  |  |  | 2%, 3 h | 94 |
| 9 |  |  |  | 2%, 3 h | 81 |
| 10 |  |  | | 2%, 3 h | 95 |

TABLE 7-continued

Pd-catalyzed Suzuki-Miyaura coupling of ArOMs with Ar'B(OH)$_2$

| entry | ArOMs | Ar'B(OH)$_2$ | product | mol % Pd | % yield[b] |
|---|---|---|---|---|---|
| 11 |  |  |  | 2%, 3 h | 97 |
| 12 |  |  |  | 2%, 3 h | 95 |
| 13 |  |  |  | 2%, 3 h | 89 |
| 14 |  |  |  | 4%, 8 h | 89 |

TABLE 8

Pd-catalyzed Suzuki-Miyaura coupling of ArOMs with Ar'B(OH)$_2$.

| entry | Het-OMs | Ar'B(OH)$_2$ | product | mol % Pd | % yield[c] |
|---|---|---|---|---|---|
| 1 |  |  |  | 2%, 3 h | 97 |
| 2 |  | | | 2%, 3 h | 91 |

TABLE 8-continued

Pd-catalyzed Suzuki-Miyaura coupling of ArOMs with Ar'B(OH)₂.

| entry | Het-OMs | Ar'B(OH)₂ | product | mol % Pd | % yield[c] |
|---|---|---|---|---|---|
| 3 | | | | 2%, 3 h | 77 |
| 4 | | | | 2%, 3 h | 91 |
| 5 | | | | 2%, 3 h | 64 |
| 6 | | | | 2%, 3 h | 85 |

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. The ligand represented by structure 1:

wherein Ar is selected from the group consisting of PH, 2-MeOC₆H₄, and 2-MeC₆H₄ and R is selected form the group consisting of hydrogen, halogen, alkyl, alkenyl, hydroxyl, PH, CY, and i-Pr.

2. The ligand of claim 1, of the structure wherein $R^1$ is selected from the group consisting of hydrogen, halogen, alkyl, alkenyl, alkynyl, hydroxyl, alkoxyl, silyloxy, amine, nitro, sulfhydryl, alkylthio, imine, amide, phosphoryl, phosphonate, phosphine, carbonyl, carboxyl, carboxamide, anhydride, silyl, thioalkyl, alkyl sulfonyl, aryl sulfonyl, seleno alkyl, ketone, aldehyde, ester, heteroalkyl, nitrite guanidine, amidine, acetral, ketal, amineoxide, aryl, heteroryl, azide, aziridine, carbanonate, epoxide, hydroxamine acid, imide, oxime, sulfonamide, thioanide, thiocarbamate, urea, and thiourea; and R is selected from the group consisting of H, 2-Me, 2-MeO, and 4-Me.

* * * * *